United States Patent [19]
Mullins

[11] Patent Number: 4,843,180
[45] Date of Patent: Jun. 27, 1989

[54] PREPARATION OF ETHERS

[75] Inventor: Michael J. Mullins, Midland, Mich.

[73] Assignee: The Dow Chemical Company, Midland, Mich.

[21] Appl. No.: 209,386

[22] Filed: Jun. 21, 1988

Related U.S. Application Data

[63] Continuation of Ser. No. 929,880, Nov. 13, 1986, abandoned, and a continuation-in-part of Ser. No. 517,548, Jul. 27, 1983, abandoned, which is a continuation-in-part of Ser. No. 368,537, Apr. 15, 1982, abandoned.

[51] Int. Cl.$^4$ ............................................... C07C 41/06
[52] U.S. Cl. ................................... 568/689; 568/673; 568/675
[58] Field of Search ..................... 568/673, 675, 689

[56] References Cited

U.S. PATENT DOCUMENTS 3,670,029  6/1972  Romanelli .

OTHER PUBLICATIONS

Commerenc et al, Bull. Soc Chim de France, 1974, 3-4, pp. 335-337 with Translation.
Weigert et al, J. Org. Chem. 1973, 38(2) pp. 335-337.
Shields et al, Chemical Comunications, 1971, pp. 193-194.
Takahashi et al I, Chem and Ind 1971, p. 488.
Takahashi et al II, Bull. Chem. Soc. Japan 45, 1972, pp. 1183-1191.

Primary Examiner—Howard T. Mars

[57] ABSTRACT

Conjugated diolefins such as 1,3-butadiene are converted to ethers by reaction with aliphatic hydroxyl-containing compounds such as ethylene glycol in the presence of a chelating phosphine adduct of zero valent nickel. A preferred chelating phosphine ligand is 1,2-bis(diphenylphosphino)ethane.

15 Claims, No Drawings

PREPARATION OF ETHERS

CROSS-REFERENCED TO RELATED APPLICATION

This is a continuation of application Ser. No. 929,880, filed Nov. 13, 1986, abandoned.

This is a continuation-in-part of application Ser. No. 517,548, filed July 27, 1983, abandoned which is a continuation-in-part of application Ser. No. 368,537, filed Apr. 15, 1982, now abandoned.

BACKGROUND OF THE INVENTION

The present invention relates to a process for converting conjugated diolefins and mixtures thereof to ethers. More particularly, the present invention comprises the process of reacting the conjugated diolefin with an aliphatic hydroxyl compound in the presence of a chelating phosphine adduct of zero valent nickel.

In Japanese Kokai No. 79/3,424, butadiene and ethylene glycol were reacted in the presence of bis(tri(o-tolyl)phosphine)palladium to prepare primarily ethylene glycol mono(2,7-octadienyl) ether and ethylene glycol di(2,7-octadienyl) ether. The catalyst was separated from the reaction mixture by super critical extraction employing ethane solvent.

In prior art processes, detrimental polymerization of alkadiene reactants, if present, cannot be avoided. Therefore, the principal products in the above reference process are not adducts of the alkadiene and the hydroxyl compound, but rather they comprise reaction products of oligomerized olefin and the hydroxyl compound.

It would be desirable to provide a process that allows the conversion of conjugated alkadienes to ethers. It would be further desirable to provide a process that allows the conversion of conjugated alkadienes to ethers while avoiding polymerization of the conjugated alkadiene. Finally, it would be desirable to provide a process for the preparation of novel unsaturated ethers having utility as solvents and cross-linking agents in polymer systems.

SUMMARY OF THE INVENTION

According to the invention there is provided a process for the preparation of unsaturated ethers corresponding to the formula:

$$(R_1R_2CO)_{\overline{n}}X \qquad , (R_1R_2CH-CR_3O)_{\overline{n}}X$$
$$\phantom{(R_1R_2CO)_{\overline{n}}X}\; \underset{CHR_3-CR_4=CR_5R_6}{|} \qquad \underset{CR_4=CR_5R_6}{|}$$

or mixtures thereof; wherein $R_1$-$R_6$ independently are selected from the group consisting of hydrogen, $C_{1-4}$ alkyl and $C_{1-4}$ alkenyl, X is the remnant of an aliphatic hydroxyl-containing compound formed by removal of the hydroxyl groups thereof, and n is an integer from one to three groups to the number of such hydroxyl groups removed from the aliphatic hydroxyl-containing compound, comprising contacting a conjugated alkadiene corresponding to the formula $R_1R_2C=CR_3-CR_4=CR_5R_6$ or a mixture thereof, with an aliphatic hydroxyl-containing compound corresponding to the formula $X(OH)_n$ wherein $R_1$-$R_6$, X and n are as previously defined at an elevated temperature in the presence of a catalyst comprising a chelating phosphine adduct of zero valent nickel.

Preferred according to the invention are chelating phosphine adducts of zero valent nickel wherein the chelating phosphine compound is of the formula $(R)_2PAP(R)_2$, where R each occurrence is $C_{1-6}$ hydrocarbyl, and A is a divalent $C_{1-10}$ group selected from alkylene, cycloalkylene, or an oxygen or nitrogen-containing aliphatic group. A preferred chelating phosphine compound is of the above formula where A is ethylene and R each occurrence is phenyl. An example of such a catalyst is a zero valent nickel complex of 1,2-bis(diphenylphosphino)ethane.

While the Applicant of the present process does not wish to be bound by any particular theory of operation of the invention, it being sufficient that the invented process gives the results described herein, it is believed that the success of the present invented process in avoiding the formation of oligomer formation of the alkadiene is due to the difunctional nature of the chelating phosphine ligands employed in the process. It is believed that the catalytic species formed in the process is a combination of at least one of the chelating phosphine ligands and a zero valent nickel moiety. The resulting catalyst is hindered so as to prevent simultaneous contact of two molecules of the conjugated alkadiene with the metal. For this reason formation of oligomers is greatly reduced. Surprisingly, the process of this invention produces the desired unsaturated monoether in selectivity of at least 60 mole percent based on the limiting reactant (usually the alkadiene) while producing the unwanted bisethers and other oligomers in a cumulative percentage of less than about 5 mole percent.

DETAILED DESCRIPTION OF THE INVENTION

The conjugated diolefins employed in the present invention are compounds of the formula:

$$R_1R_2C=CR_3-CR_4=CR_5R_6$$

wherein $R_1$-$R_6$ independently are selected from the group consisting of hydrogen, $C_{1-4}$ alkyl and $C_{1-4}$ alkenyl.

Preferred conjugated diolefins are 1,3-butadiene and 1,3-pentadiene.

The conjugated diolefin may be present in relatively pure form or as a mixture with other saturated and unsaturated aliphatics.

The aliphatic hydroxyl-containing compounds suitable for use in the invention are mono-, di- or trihydric according to the number of hydroxyl compounds present in the compounds, and primary, secondary or tertiary according to the number of hydrogen atoms attached to the carbon atom adjacent to the OH group. Preferred aliphatic hydroxyl-containing compounds are $C_{1-6}$ alkanols or vicinal alkylene glycols. Especially preferred is ethylene glycol. Accordingly, the above aliphatic hydroxyl-containing compounds corresponding to the formula $(OH)_n$ wherein X and n are as previously defined.

The catalyst according to the present invention may be prepared by known techniques, for example, according to the procedures outlined by P. W. Jolly et al., *The Organic Chemistry of Nickel,* Vol. 1, Chapt. 3, Academic Press (1974), which teaching is incorporated herein by reference in its entirety. The catalyst may be employed in any amount sufficient to catalyze the process, preferably, an amount from about 0.1 percent to about 10 percent by weight based on the hydroxyl-containing compound.

The reaction is conducted at a temperature from about 20° C. to about 150° C., preferably from about 100° C. to about 130° C. At lower temperatures, less than about 100° C., the reaction rate tends to diminish. At elevated temperatures, above about 150° C., the catalyst tends to degrade due to thermal instability.

The reaction may be conducted at elevated or reduced pressures. Suitable pressures are from about 1 torr to about 500 psig and depends primarily on the partial pressure attributed to the conjugated alkadiene and alcohol reactants.

The reactants may be combined in any order and in nearly any ratio. Equivalent ratios of hydroxyl compound to conjugated diolefin from about 100:1 to 0.1:1 may be employed. However, higher ratios of hydroxyl reactant to conjugated diolefin tend to promote the formation of desired ether products.

The reaction is preferably conducted in a solvent suitably chosen to dissolve both reactants and to be unreactive and stable under the reaction conditions employed. Such solvents include polar aprotic compounds such as tetrahydrofuran and (poly)alkylene glycol diethers such as 1,2-dimethoxy ethane, triethylene glycol dimethyl ether, etc.

According to the invention, it has been found that such difficultly etherizable conjugated alkadienes as 1,3-butadiene or 1,3-pentadiene may be reacted with hydroxyl compounds exemplified by methanol ethylene glycol in surprisingly high selectivities and conversions, particularly avoiding the formation of undesirable amounts of oligomeric products. In preferred embodiments, such conversions are at least about 40, most preferably at least about 50 mole percent with selectivities to the desired monoether of at least about 60, most preferably at least about 70 mole percent, said percentages being based on the moles of the limiting reactant (usually the diene). In such preferred embodiments, the total amount of the undesirable bisethers and other oligomers formed is at a level less than 15 mole percent, most preferably less than 10 mole percent. Because of the unique ability of the invented process, it is possible for the first time to prepare certain novel unsaturated ethers that may suitably be employed as cross-linking agents in polymeric systems. Illustrative of such novel ethers are the reaction products of 1,3-pentadiene and ethylene glycol, e.g., 2-(2-hydroxyethoxy)-2-pentene.

Such unsaturated ethers as are formed, for example, by reaction of 1,3-butadiene or 1,3-pentadiene with an alkylene glycol such as ethylene glycol may be hydrogenated in known manner to known saturated glycol monoethers for use in solvents, etc. For example, sec-butyl and n-butyl monoethers of ethylene glycol are easily prepared by this method of reacting 1,3-butadiene with ethylene glycol and hydrogenating over a noble metal catalyst such as platinum. The isomers are initially prepared in about a 2:1 molar ratio with the predominant product being the sec-butyl monoether. This process is schematically illustrated as follows:

CH₂=CH—CH=CH₂ + HOCH₂CH₂OH ⟶

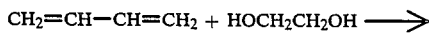
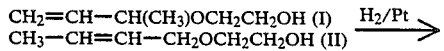

-continued
sec-butyl-OCH₂CH₂OH + n-butyl-OCH₂CH₂OH.

Alternatively, certain novel diethylenically unsaturated ethers may be prepared by the invented process upon reaction of two equivalents of the diolefin with one equivalent of the alkylene glycol. In this manner an oligomeric mixture of the bis ethers:

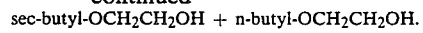

and

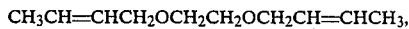

e.g., 1-(2-butenyloxy)-2-(1-methylallyloxy)ethane, 1,2-di(1-methylallyloxy)ethane, and 1,2-di(2-butenyloxy)ethane may be prepared by continued reaction under the same reaction conditions initially described. These novel bis ethers may optionally be prepared by standard chemical processes from the monoethers. For example they could also be prepared by the known reaction of the monoether with a chlorinated alkene in the presence of an alkyl metal compound, e.g., n-butyl lithium. These unique diunsaturated diethers may be hydrogenated as previously described to form the corresponding saturated diethers or employed as cross-linking agents by making use of the polymerizable ethylenic functionalities. These compounds and their preparation are further described in following Example 1.

SPECIFIC EMBODIMENTS

Having described the invention, the following examples are provided as further illustrative and are not to be construed as limiting.

EXAMPLE 1

Addition of Ethylene Glycol to Butadiene

A 200-ml bomb was charged with ethylene glycol (18.0 g, 0.29 mole), tetrahydrofuran (25 ml), Ni[1,5-dyclooctadiene]₂ (300 mg, 0.001 mole) and 1,2-bis(diphenylphosphino)ethane (0.80 g. 0.002 mole) under an argon atomsphere. The reaction mixture turned dark red-orange indicating the formation of Ni[φ₂PCH₂CH₂Pφ₂]₂. The bomb was then sealed and weighed. After weighing the bomb was connected to a source of butadiene and cooled to −78° C. to condense butadiene inside the bomb. After reweighing, it was found that 9.7 g (0.18 mole) of butadiene had condensed inside.

The bomb was then connected to the appropriate vents and blow-down lines inside a safety cubicle and heated to 120° C. for 22 hours. Initial pressure of about 180 psi diminished to about 120 psi during the course of the reaction. After the indicated time period, the bomb was cooled, vented and opened. The contents were removed by washing with tetrahydrofuran. Upon exposure to air, the orange-colored solution turned pale green.

A small portion of the product solution (28.8 g of 78.2 g total) was evaporated and distilled. Material having a boiling point range from 45° C. to 60° C. at 3 torr was retained (2.88 g, >95 percent pure 69 percent yield based on glycol). The product comprised primarily the 1-methylallyl and 3-methylallyl monoethers of ethylene glycol in the weight ratio of about 2:1. Product identity was confirmed by proton and carbon nuclear magnetic resonance spectra and by infrared spectroscopy. Further analysis of the reaction mixture indicated about 5 percent by weight of an isomeric mixture of the bis-butenyl ethers of ethylene glycol were also formed. These bis-butenyl ethers were identified as 1-(2-butenyloxy)-2-(1-methylallyloxy)ethane, 1,2-di(1-methylallyloxy)ethane and 1,2-di(2-butenyloxy)ethane.

EXAMPLE 2

The reaction conditions of Example 1 were substantially repeated employing the following chemicals in the indicated amounts: Ni[1,5-cyclooctadiene]$_2$ (300 mg, 1.1 mmole), triethylphosphine (1.0 g, 8.5 mmole), ethylene glycol (7.8 g, 125 mmole), 1,3-pentadiene (8.6 g, 125 mmole) and tetrahydrofuran (25 ml). The reaction was conducted at 140° C. for 16 hours. Analysis by gas chromatography indicated formation of the desired product 2-(2-hydroxyethoxy)-3-pentene, 27 percent conversion based on ethylene glycol, 66 percent selectivity. By-products comprised mostly pentadiene dimers.

EXAMPLE 3

Comparative Nonchelating Phosphine Ligand

The reaction conditions of Example 1 were substantially repeated employing the zero valent nickel phosphine catalyst Ni[PEt$_3$]$_4$. The weight ratio of ethylene glycol to butadiene reactants was 1:1.56. Analysis of the reaction mixture after heating for 16 hours at 100° C. indicated only a 7 percent yield of the 1-methylallyl and 3-methylallyl monoethers of ethylene glycol present in a molar ratio of about 1:1.6. In contrast to the results of Example 1, large amounts of oligomerized butadiene by-products were present in the reaction mixture. The reaction conditions of Example 1 were again substantially repeated employing the phosphite complexes of zero valent nickel, Ni[P(OR)$_3$]$_4$, where R is phenyl or ethyl. After reaction for 16 hours at temperatures of about 120° C., the reaction mixtures were found to contain oligomerized butadiene. No ether products were detected.

EXAMPLE 4

Comparative—Rhodium Catalyst

The reaction conditions of Example 1 were again substantially repeated employing rhodium tris(triphenylphosphine)chloride catalyst. No ether reaction products were detected.

EXAMPLE 5

Comparative—Chelating Phosphine Ligand Omitted

When a sample of nickel bis(1,5-cyclooctadiene) was heated in the presence of the reactants employed in Example 1, the compound decomposed yielding elemental nickel.

EXAMPLE 6

Synthesis of 3-Methoxybut-1-ene and 1-Methoxybut-2-ene

A 500-ml autoclave made of 316 stainless steel is charged with the following in an argon atmosphere: methanol (100 ml, 2.47 moles), 1,2-bis(diphenylphosphino)ethane (800 mg, 2.01 mmoles), bis(1,5-cyclooctadiene nickel (300 mg, 1.09 mmoles) and t-butylbenzene (1.000 g), used as an internal standard for quantitative gas chromatographic analysis. About 5 g of butadiene is added to the autoclave before heating to 120° C. A total of 26.03 g (0.481 mole) of butadiene is added, maintaining the pressure between 140 and 170 psig. The butadiene is completely converted (>95 percent) within 5 hours. Analysis by gas chromatography indicates 100 percent selectivity within experimental error (±5 percent) for a mixture (1.60 to 1, branched to linear, 43.3 g) of the title compounds.

EXAMPLE 7

Large-Scale Synthesis of 3-Methoxybut-1-ene and Methoxybut-2-ene

A 2-gallon glass-lined reactor, equipped with a catalyst supply tank, butadiene supply tank, nitrogen supply, vent line, safety pressure frangible, stirrer, temperature and pressure monitors, filler pipe and bottom drain is used. Three liters (2375 g, 74.2 moles) of methanol is drawn into the reactor via polyethylene tubing. After purging with nitrogen, 11 g of Ni[1,5-cyclooctadiene][1,2-bis(diphenylphosphino)ethane] catalyst dissolved in 100 ml of toluene is added. Butadiene (663 g, 11.4 moles, 93 percent by weight purity, remainder vinyl cyclohexane) is then admitted, until the reactor pressure at 100° C. is 155 psig. The temperature is maintained overnight. About one-half of the butadiene consumption occurs in the first hour, and >95 percent conversion occurs in the first 8 hours.

The product is isolated by washing the crude material with ice water to remove most of the excess methanol followed by distillation. A total of 791 g of butenyl methyl ethers (9.20 moles, 81 percent yield and >81 percent selectivity based on butadiene) is obtained.

What is claimed is:

1. A process for the preparation of unsaturated ethers corresponding to the formula:

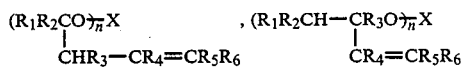

or mixtures thereof; wherein $R_1$–$R_6$ independently are selected from the group consisting of hydrogen, $C_{1-4}$ alkyl and $C_{1-4}$ alkenyl, X is the remnant of an aliphatic hydroxyl-containing compound formed by removal of the hydroxyl group thereof, and n is one comprising contacting a conjugated alkadiene corresponding to the formula $R_1R_2C=CR_3-CR_4=CR_5R_6$ or a mixture thereof, with an aliphatic hydroxyl-containing compound corresponding to the formula $X(OH)_n$ wherein $R_1$–$R_6$, X and n are as previously defined at an elevated temperature in the presence of a catalyst consisting essentially of a chelating phosphine adduct of zero valent nickel under conditions sufficient to form the unsaturated ether in a yield of at least 60 mole percent based on the limiting reactant and to prevent the formation of oligomers including bisethers in a total amount greater than 5 mole percent based on the limited reactant.

2. The process according to claim 1 wherein the formation of reaction products of oligomers of the conjugated alkadiene and the aliphatic hydroxyl-containing compound is substantially avoided.

3. The process of claim 1 wherein the chelating phosphine compound is of the formula $(R)_2PAP(R)_2$ where R each occurrence is $C_{1-6}$ hydrocarbyl, and A is a divalent $C_{1-10}$ group selected from alkylene, cycloalkylene or an oxygen or nitrogen-containing aliphatic group.

4. The process of claim 3 wherein A is ethylene and R each occurrence is phenyl.

5. The process of claim 4 wherein the catalyst is formed by contacting Ni[1,5-cyclooctadiene]$_2$ and 1,2-bis(diphenylphosphino)ethane.

6. The process of claim 1 wherein the conjugated alkadiene is present as a mixture with other saturated and unsaturated aliphatic compounds.

7. The process of claim 1 wherein the conjugated alkadiene is 1,3-butadiene or 1,3-pentadiene.

8. The process of claim 1 wherein the aliphatic hydroxyl-containing compound is a $C_{1-6}$ alkanol or vicinal alkylene glycol.

9. The process of claim 8 wherein the aliphatic hydroxyl-containing compound is ethylene glycol.

10. The process of claim 1 wherein the temperature of the reaction is from about 20° C. to about 150° C.

11. The process of claim 10 wherein the temperature is from about 100° C. to about 130° C.

12. The process of claim 1 wherein the alkadiene is butadiene, the aliphatic hydroxylcontaining compound is methanol and the unsaturated ether is a mixture of 3-methoxybut-1-ene and 1-methoxybut-2-ene.

13. The process of claim 12 wherein the chelating phosphine adduct is an adduct of 1,2-bis(diphenylphosphino)ethane and bis(1,5-cyclooctadiene nickel).

14. The process of claim 13 wherein more than 95 mole percent of the butadiene is converted to the unsaturated ether in a percent selectivity of at least 95 percent based on butadiene.

15. The process of claim 13 wherein more than 95 mole percent of the butadiene is converted to the unsaturated ether in a percent selectivity of greater than 81 percent based on butadiene.

* * * * *